(12) United States Patent
Walsh et al.

(10) Patent No.: US 8,372,341 B2
(45) Date of Patent: Feb. 12, 2013

(54) ASSAY DEVICE PROCESSING APPARATUS AND METHOD

(75) Inventors: Aiden John Walsh, County Antrim (GB); Stephen Peter Fitzgerald, County Antrim (GB)

(73) Assignee: Randox Laboratories Ltd., Antrim (GB)

( * ) Notice: Subject to any disclaimer, the term of this patent is extended or adjusted under 35 U.S.C. 154(b) by 402 days.

(21) Appl. No.: 12/087,653

(22) PCT Filed: Jan. 25, 2007

(86) PCT No.: PCT/GB2007/000247
§ 371 (c)(1),
(2), (4) Date: Sep. 11, 2008

(87) PCT Pub. No.: WO2007/085831
PCT Pub. Date: Aug. 2, 2007

(65) Prior Publication Data
US 2009/0053824 A1  Feb. 26, 2009

(30) Foreign Application Priority Data
Jan. 27, 2006 (GB) .................................. 0601707.3

(51) Int. Cl.
*C12Q 1/68* (2006.01)
*G01N 21/00* (2006.01)
*G01N 15/06* (2006.01)
*B01L 3/02* (2006.01)
*B01L 9/00* (2006.01)
*B01D 11/02* (2006.01)

(52) U.S. Cl. ................. 422/65; 422/50; 422/62; 422/63; 422/66; 422/68.1; 422/81; 422/515; 422/521; 422/526; 422/560; 422/565; 422/268; 422/300

(58) Field of Classification Search ........... 422/63–68.1, 422/50, 81, 501, 509–511, 515, 516, 521, 422/525, 526, 560, 565–567, 268, 300, 104; 436/180
See application file for complete search history.

(56) References Cited

U.S. PATENT DOCUMENTS

| | | | |
|---|---|---|---|
| 6,669,432 B2 * | 12/2003 | Hamel et al. ............. | 414/331.05 |
| 2004/0191890 A1 * | 9/2004 | Meyer et al. ............... | 435/287.2 |
| 2004/0202580 A1 | 10/2004 | McEntee | |

FOREIGN PATENT DOCUMENTS

| | | |
|---|---|---|
| EP | 0 994 355 A1 | 4/2000 |
| EP | 1 302 244 A1 | 4/2003 |
| WO | WO 2004/034014 A2 | 4/2004 |

* cited by examiner

*Primary Examiner* — Jill Warden
*Assistant Examiner* — Dean Kwak
(74) *Attorney, Agent, or Firm* — Oliff & Berridge, PLC (57) ABSTRACT

Assay device processing apparatus includes a rotatably mounted assay device vessel support; and a drive for rotating the support. The support is rotatable about a substantially horizontal first axis so that, upon rotation, an assay device vessel attached to the support can be inverted.

22 Claims, 8 Drawing Sheets

ASSAY DEVICE PROCESSING APPARATUS AND METHOD

The invention relates to an assay device processing apparatus and a method for processing assay devices such as biochips.

Such assay devices typically have an array of localised reactive sites containing different reactive species, for example different antibodies, deposited thereon.

In EP-A-0994355 we describe an assay device processing instrument having a number of different processing modules connected together by a transport system. One of these modules is a wash module which enables biochips in a vessel to be washed so as to remove unbound sample and reagents, the wash fluid subsequently being removed. The module also includes a shaker system which can shake the vessel during the washing process.

It is also often desirable to prevent the surface of the assay device from drying out after washing, for example to maintain a relatively uniform film of liquid across the surface of the assay device which is sufficient to prevent drying at the binding site and damage to bound molecules. A certain degree of wetness is also necessary to maintain the integrity of the newly bound material prior to the addition of chemiluminescent or other signal reagents or of reagents before an additional incubation step.

A limited attempt at solving this problem is described in US-A-2002/0064774 in which the assay device is rotated about its axis, the device being maintained horizontal so as to achieve an even distribution of materials. However, this is not suitable for use as a washing module.

In accordance with a first aspect of the present invention, an assay device processing apparatus comprises a rotatably mounted assay device vessel support; and a drive for rotating the support, the support being rotatable about a substantially horizontal first axis so that, upon rotation, an assay device vessel attached to the support can be inverted.

In accordance with a second aspect of the present invention, a method of processing an assay device in an assay device vessel containing a liquid and attached to a support of apparatus according to the first aspect of the invention comprises rotating the vessel about the first axis.

We have devised a new type of apparatus in which the assay device vessel is rotated about a horizontal first axis. This has a number of advantages.

During a wash process, the assay device vessel can be rotated to and fro about the first axis while retaining liquid in the vessel, constituting a soaking step. Additionally, or alternatively, the assay device vessel can be inverted thus allowing waste and other materials to be dispersed or removed.

Further, the assay device vessel can be spun, for example at the end of a washing sequence, to ensure removal of all waste and other materials. This should be contrasted with the conventional use of aspiration probes which can cause fast flow across the assay device surface towards the aspiration points and this can create shear forces and cause damage to the binding sites, particularly of weakly bound molecules. Also, flow close to the surface may modify the concentration effectively reversing the binding reactions. Therefore significant care can be required in the positioning and operation of the aspiration probes close to the biochip surface. In contrast, the invention enables a gentle washing process to be undertaken which could allow reactions involving less strongly bound molecules to be addressed—ranging from strong covalent, electrostatic, hydrogen to even weaker bonds. The more effective removal of sample, reagents and wash fluid from the biochip and vessel can allow wash times including rinse and soak to be reduced—helping to speed up the assay process and increase throughput. More efficient usage of wash fluids is also achieved thereby reducing storage requirements or replenishment frequency for wash fluids and also fluid waste storage if appropriate.

It will be appreciated that during inversion for waste dispersal or removal, the speed of rotation, angle turned through and the angular acceleration and deceleration are consistent not only with fluid removal from each individual vessel or well but also that these fluids subsequently do not reach and possibly contaminate adjacent or other vessels and particularly the biochip surface. This is similarly important during spinning.

Spinning of the vessel has been found to automatically leave behind a thin uniform film of liquid on the surface of the biochip within the vessel. The thickness and degree of uniformity (i.e. variation in thickness of the fluid layer across the surface) are dependent on surface and fluid properties, the rotation speed and distance from the axis of rotation.

The spinning process will normally take place at the end of a washing cycle prior to the transfer of the vessel to another module for further processing such as the addition of a signal reagent or other reagent prior to a further incubation phase. However, the spinning process could also be used between wash steps.

In the preferred apparatus, the support is movable between a processing station at which one or more liquids can be supplied to the vessel, and a waste removal station at which the support can be rotated to allow waste liquid(s) to dispense. This separates out the positions at which liquids and reagents are supplied to the vessel from the position at which waste liquids are removed. It also makes it easier to handle the waste liquids by providing specific disposal systems.

The support could be translated from the processing station to the waste removal station but conveniently the support is also mounted for rotation about a vertical second axis to move from the processing station to the waste removal station.

In order to constrain liquid as it disperses from the vessel, the waste removal station preferably includes a protective housing within which the support is rotated in use about the first axis.

The internal shape, particularly the roof, of the protective (or waste capture) housing may be chosen to ensure that waste runs around the inside of the roof and sidewalls and does not drip into the vessel possibly contaminating the assay device.

For example, the roof shape and material can chosen to ensure that the fluid thrown from the biochip vessel or well adheres initially to the surface of the roof and runs down the roof and walls rather than forms an enlarging drop on the lower surface of the roof which could fall onto the surface of a biochip. Contamination of the biochip surface and incorrect analysis could result. Having a roof which is inclined over the complete vessel helps to achieve this.

In addition or alternatively, stopping the vessel in an upside down position whilst within or being transferred to or from the 'spinning/waste removal' section helps to minimise the possibility of contamination.

Conveniently, the assay device vessel is at least removed in its inverted state from the waste removal station to reduce the possibility of dripping into the vessel.

When the vessel is spun in the waste removal station, we have found that a relatively even spread of waste is deposited on the upper sidewall and roof of the protective housing.

Typically, one or more dispense probes are provided at the processing station for supplying wash fluid and reagents to the vessel. If preferred, the dispense probes can be maintained at a height above the level of liquid in the vessel so as not to come into contact directly or indirectly with waste products such as sample and reagents. The height of the dispense probes and speed of flow therethrough can be adjusted to ensure that splashing is reduced/eliminated and that the fluid flow into/within the vessel does not damage the assay device surface and bound molecules.

Aspiration probes can also be used if appropriate, particularly alongside the dispense probes to ensure that the assay device vessel does not overflow during a dispense process. However, aspiration probes would not be required if precise volumes were dispensed into the vessel. The use of aspiration probes for overflow control also allows a degree of fluid flow or circulation within the vessel which may be beneficial during the washing process.

An example of a method and apparatus according to the present invention will now be described with reference to the accompanying drawings, in which.

The module to be described processes an array of biochip storage wells or vessels mounted on a carrying tray. We will therefore describe an example of such an array and tray first.

Figure 1:
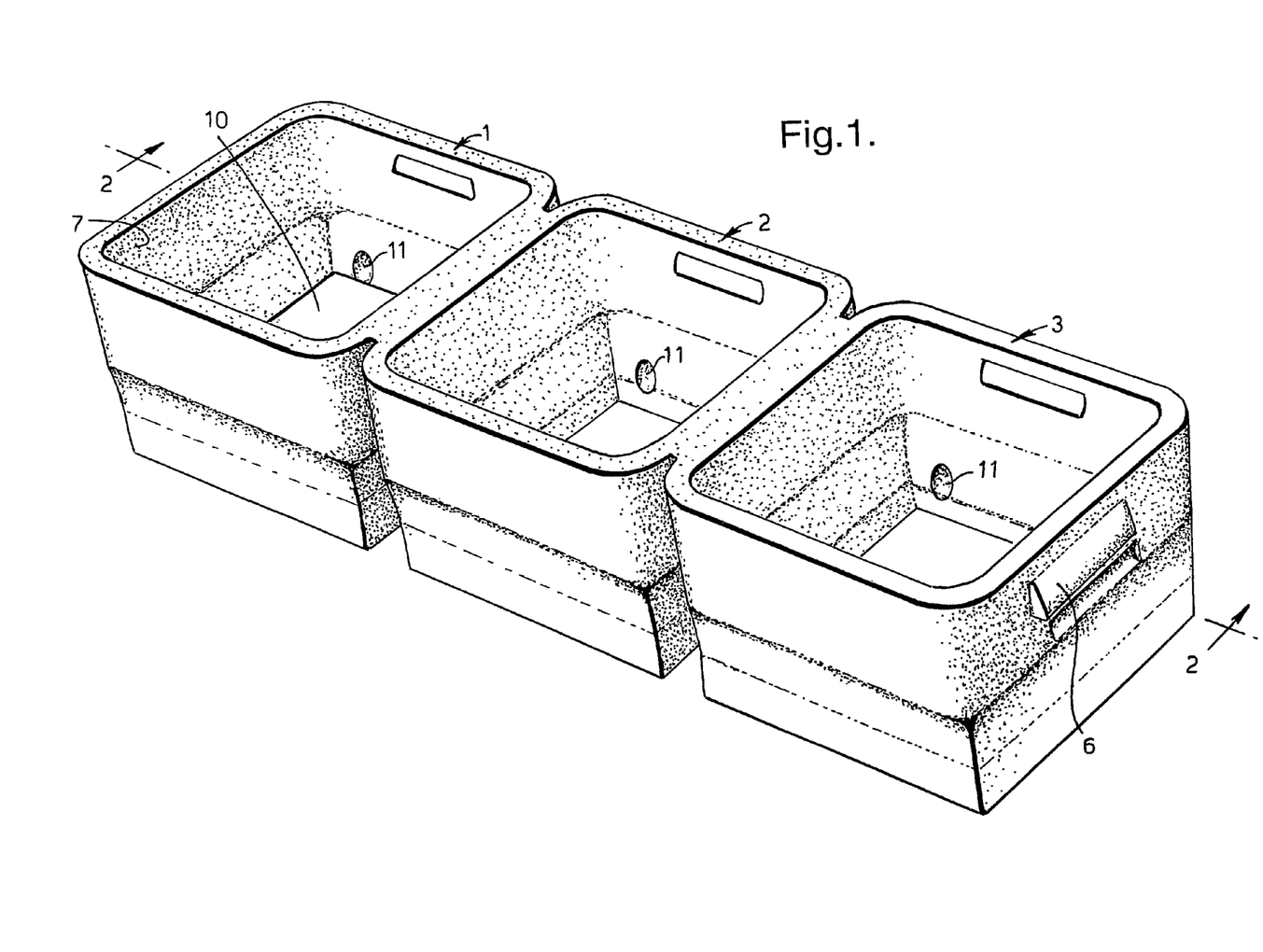
FIG. 1 is a perspective view of an array of biochip storage wells from above.
Figure 2:
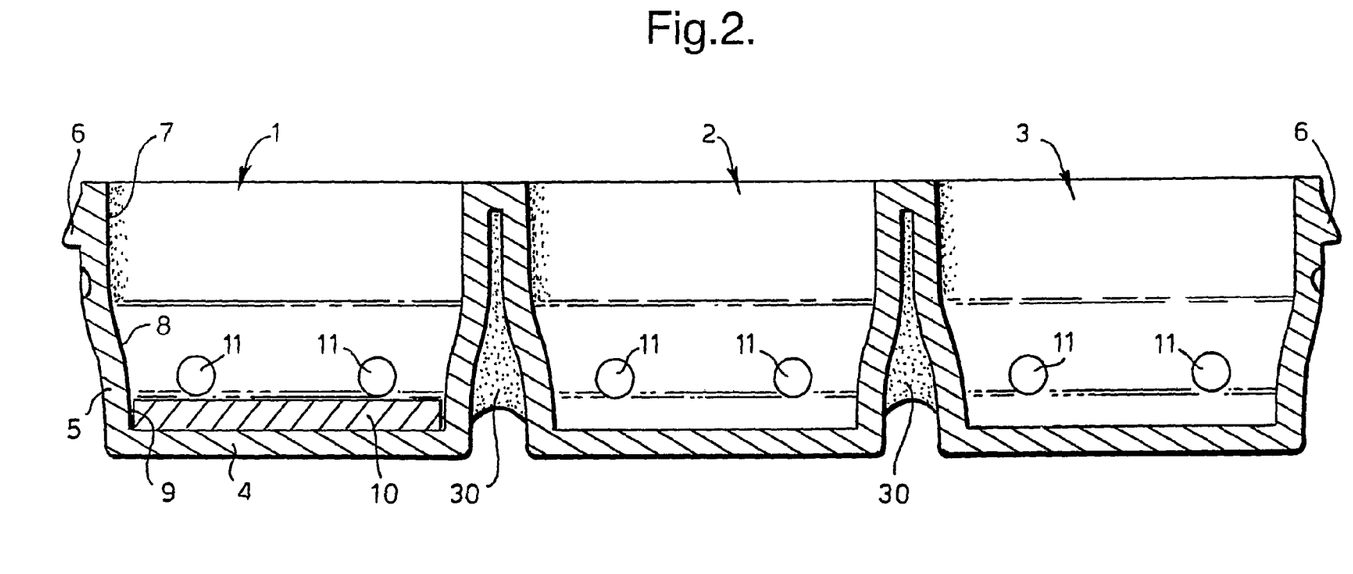
FIG. 2 is a section taken on the line 2-2 in FIG. 1 but showing a biochip in one of the storage wells.

FIG. 1 illustrates an array of three storage wells 1-3 formed from a one-piece plastics moulding of P.V.C. or polypropylene. The plastics material incorporates a black pigment. Each storage well 1-3 has a similar form and as can be seen in FIG. 1 is substantially square in plan. For convenience, only the storage well 1 will be described in detail.

The storage well 1 has a base 4 and a sidewall 5 surrounding the base. As can be seen in FIG. 2, the sidewalls 5 of each storage well are integrally formed at the junctions between the storage wells.

Protrusions 6 are moulded at each end of the array to enable the array to be handled easily.

Each sidewall 5 has an upper section 7 which is substantially vertical with respect to the base 4 and a lower section 8 which tapers inwardly. The taper terminates just short of the base 4 so as to define a region 9 having a width and height corresponding to that of a biochip 10. Typical array dimensions are: 42 mm long, 9 mm high and 14 mm wide at the top.

Figure 3:
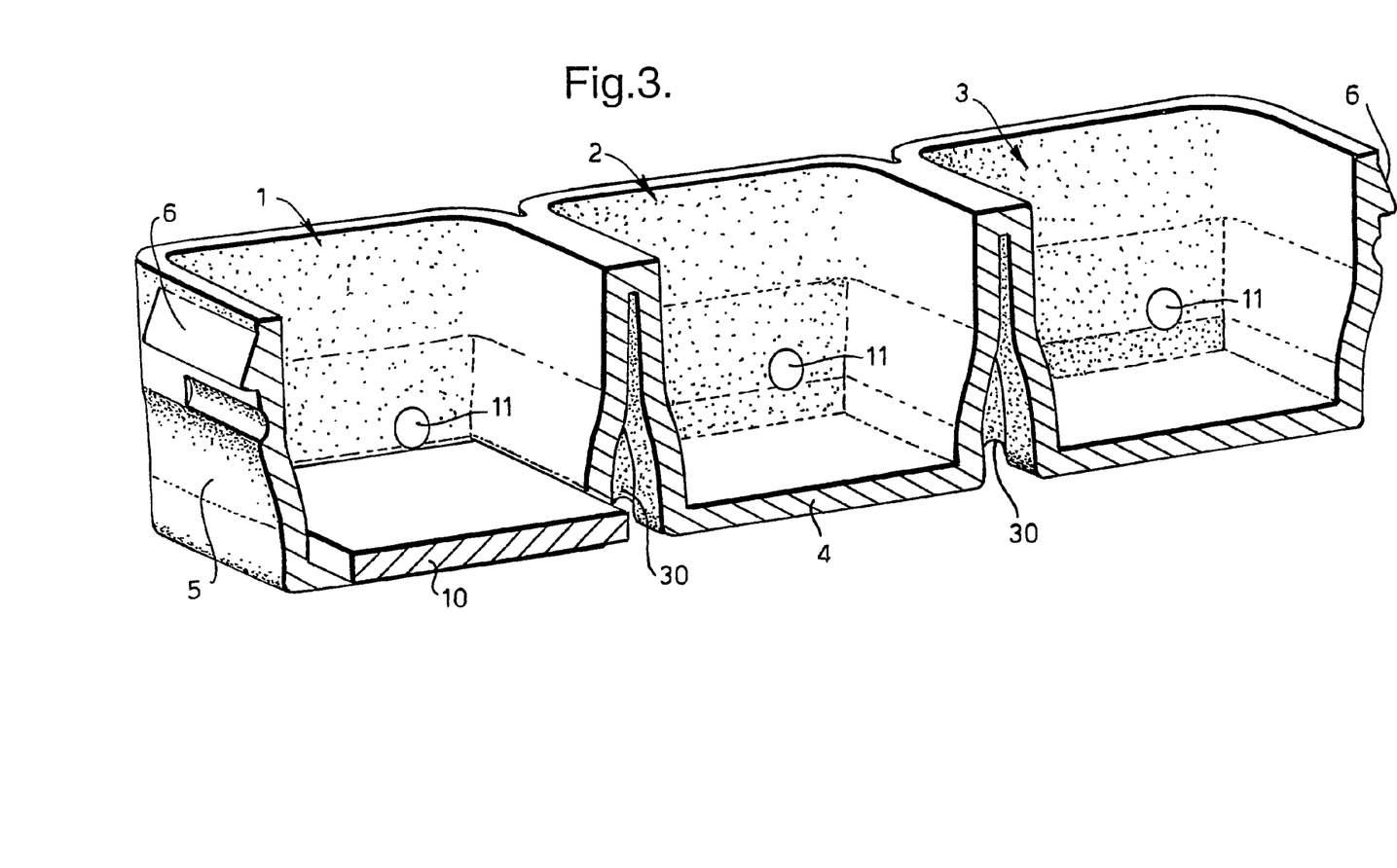
FIG. 3 is a perspective view of the section shown in FIG. 2.

Following construction of the array of storage wells 1-3, each is supplied with a biochip 10. The biochips 10 can be prepared in any conventional manner so as to attach ligands on respective reaction sites. For example, ligands could be immobilized by means of microfluidic dispensing of the ligand onto the substrate, which is chemically activated. Alternative chemical or physical methods could be used. It is important that the method of immobilisation, e.g. covalent immobilisation, is such that ligands are not released during incubation and washing steps. Each chip which typically has dimensions 9 mm×9 mm and is about 0.6 mm thick is then dropped into the respective storage well 1-3 and one such biochip 10 is shown in the storage well 1 in FIGS. 2 and 3.

Each biochip 10 is then secured in the base of the storage well by cold or hot forming bumps 11 on at least one side section of the sidewall 5. These bumps may be either preformed for press fitting or post-formed after insertion of the biochip 10.

As well as being tapered, the inner surfaces of the sidewalls 5 are preferably provided with a polished finish to reduce the curvature of the liquid meniscus and minimise optical aberrations.

Figure 4:
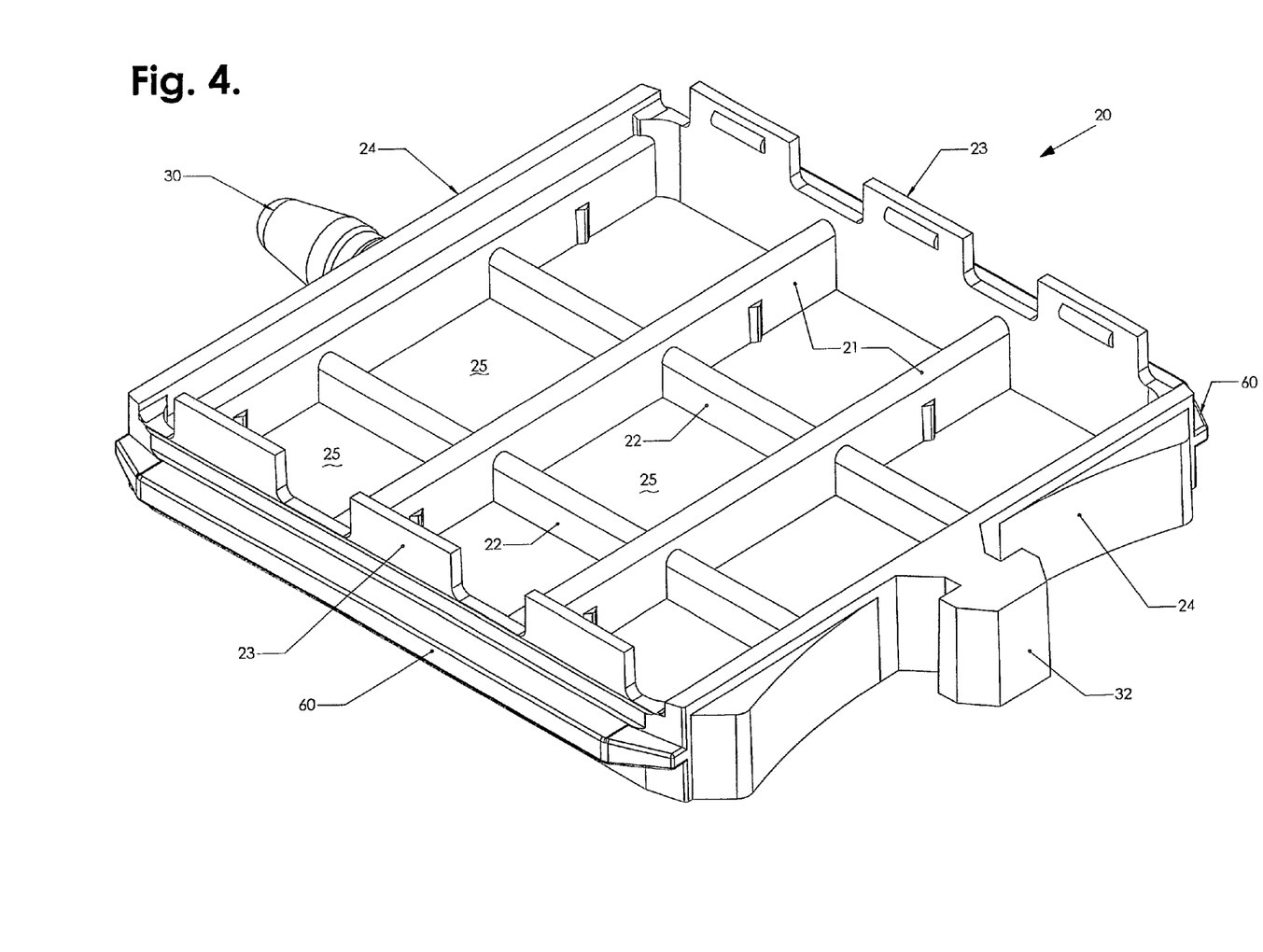
FIG. 4 is a perspective view of a carrying tray for the array of storage wells.

Following these steps, the set of three storage wells can then be prepacked in an individual sealed "bubble" on a tape forming a roll for reel dispensing. However, in the preferred approach, three sets of storage well arrays of the type shown in FIG. 2 are loaded onto a carrying tray 20 as shown in FIG. 4. This carrying tray is made of a plastics moulding and has two sets of crossbars 21,22 extending between opposite sidewalls 23,24 respectively. Nine openings 25 are defined into which the respective storage wells can be located. Each set of three storage wells 1-3 is loaded parallel to the crossbars 21 with the crossbars 22 entering into corresponding recesses 30 between adjacent storage wells. The loaded carrier tray is then sealed in suitable packing materials for transportation. The user can then either remove the storage wells from the carrier tray or, as in the present case, leave them in place and use the carrier tray to move the storage wells about the immunoassay process, for example as described in more detail in EP-A-0994355.

In another case, the biochips 10 can be glued into the respective storage wells.

The carrying tray 20 includes a Bal catch 30 to enable it to be secured to different processing modules including the module to be described below and a boss 32 for attachment to a transport system (not shown).

Figure 5:
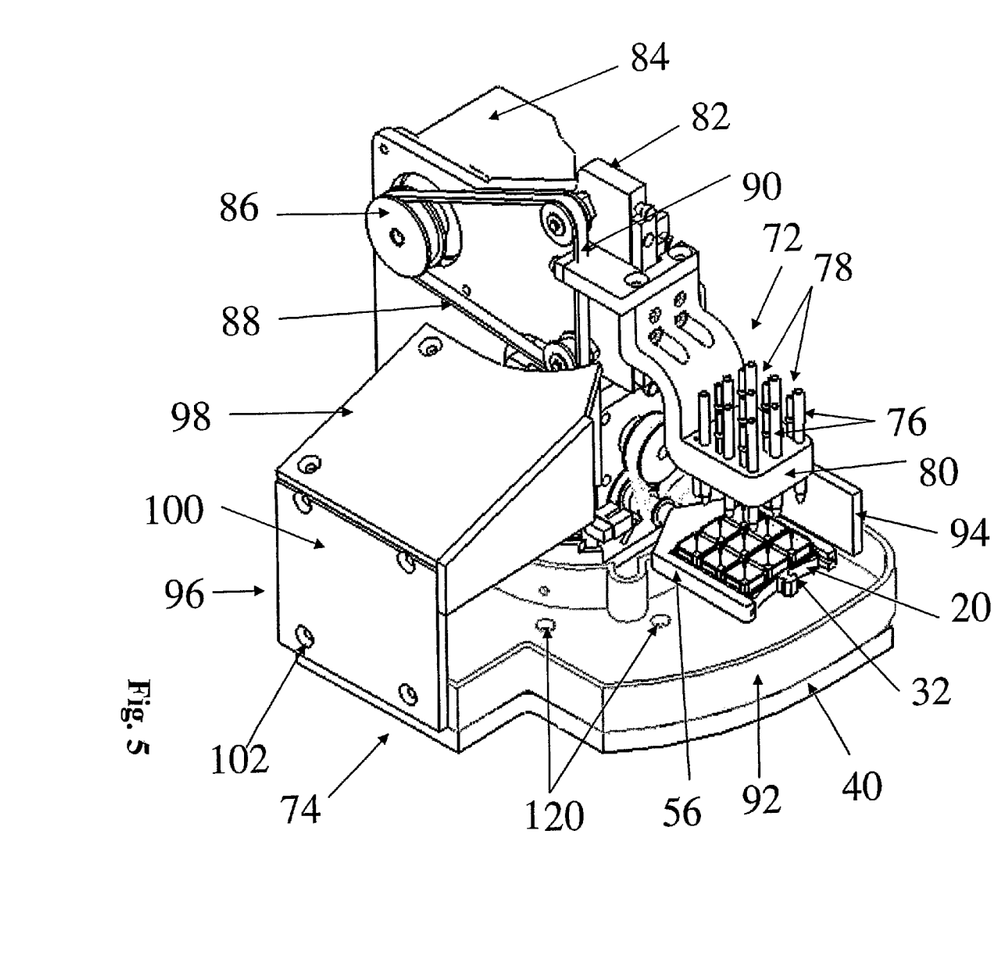
FIG. 5 is a perspective view of the apparatus from one side and above.
Figure 6:
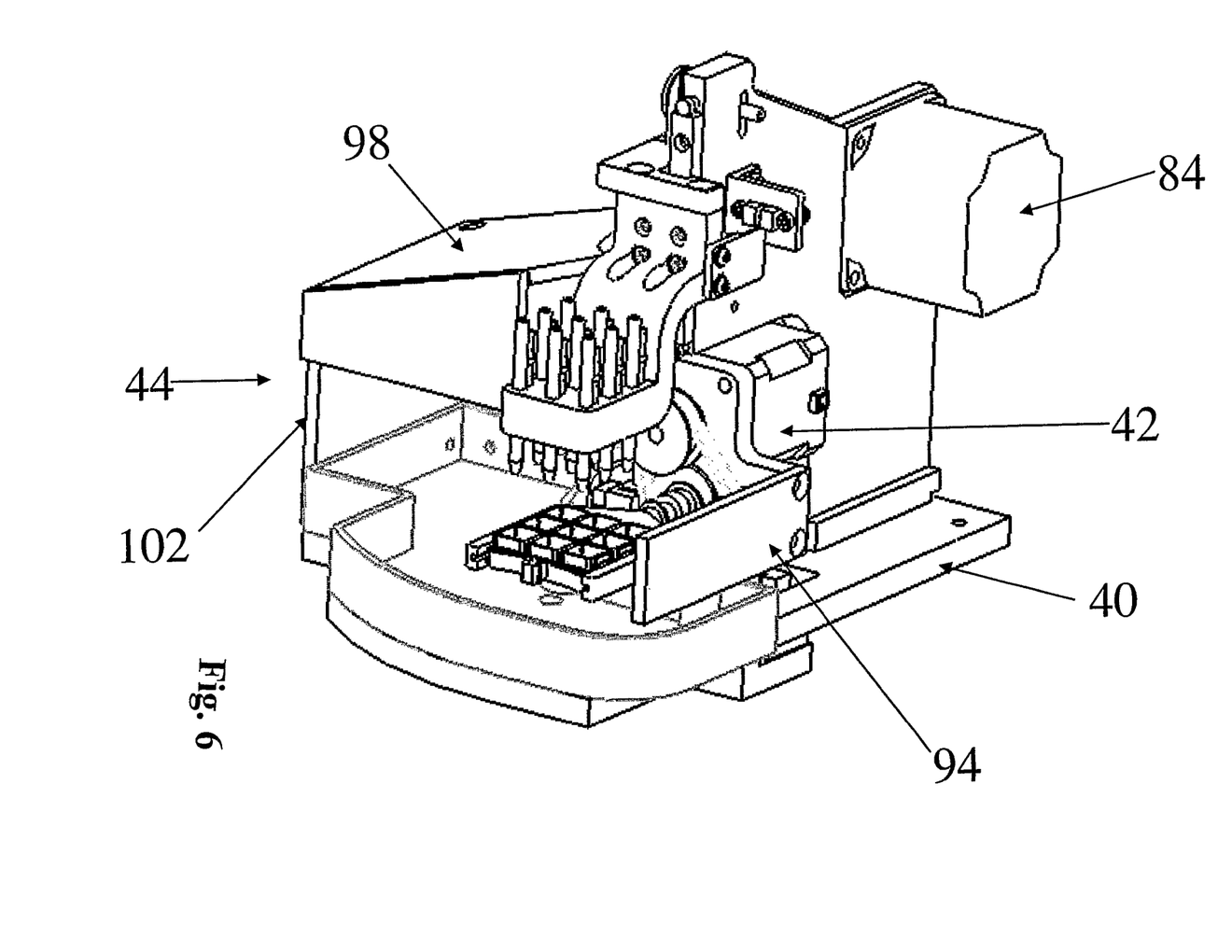
FIG. 6 is a perspective view of the apparatus from the other side and above.
Figure 7:
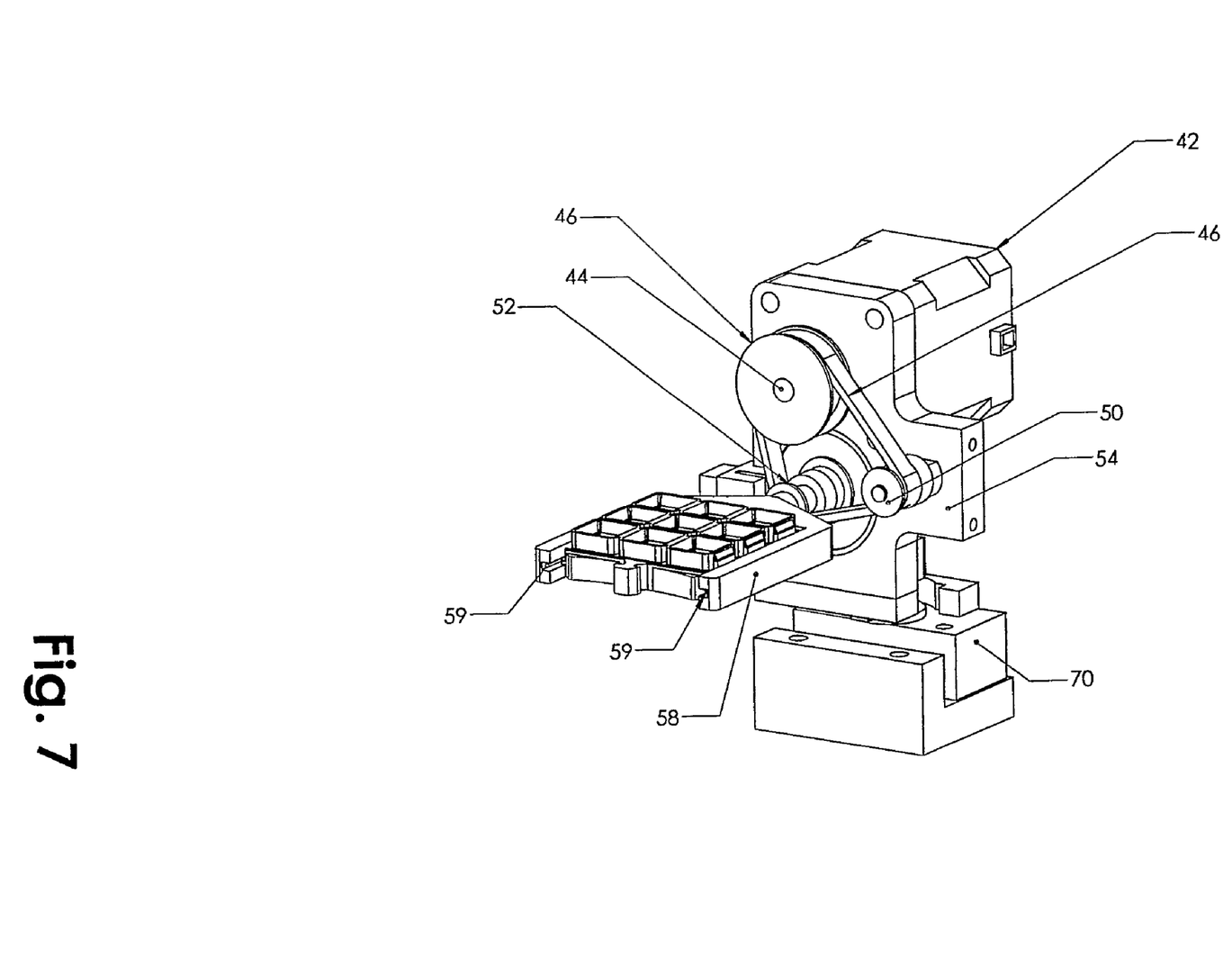
FIG. 7 is a perspective view of the spinning mechanism in more detail.

FIGS. 5 to 7 illustrate an example of a processing module according to the invention. The module comprises a base plate 40 on which is mounted a first stepper motor 42 having a drive spindle 44 secured to a drive pulley 46.

A drive belt 48 is entrained about the drive pulley 46, an idler pulley 50 and a rotatably mounted socket 52, the pulleys 46,50,52 being mounted to an upstanding support plate 54 to which the stepper motor 42 is also mounted.

The socket 52 receives a spigot 56 of a U-shaped well holder 58. As seen in FIG. 7, the arms of the well holder 58 are provided with elongate grooves 59 which receive respective flanges 60 (FIG. 4) of a carrying tray 20, the tray being locked to the holder 58 via the BAL catch 30.

When the stepper motor 42 is actuated, rotational drive is communicated to the socket 52 via the drive belt 48 causing the well holder 58 and carrying tray (and biochip wells) to be rotated about a first, horizontal axis. As will be explained in more detail below, this rotation can be a simple rocking motion to and fro or the entire carrying tray 20 could be inverted. Furthermore, the stepper motor 42 can cause the well holder 58 to be spun at high speed.

The plate 54 is rotatably mounted about a vertical axis to the base plate 40 and can be rotated about the vertical axis by a pneumatic actuator 70 mounted beneath the plate. This enables the spinning mechanism shown at FIG. 7 to be rotated between a processing station 72 (as shown in FIG. 5) and a waste removal station 74.

At the processing station 72, a set of dispense probes 76 and a set of aspirator probes 78 are mounted to a support member 80 which is slidably mounted for vertical movement to a support plate 82. Slidable movement up and down the support plate 82 is achieved by suitably controlling a stepper motor 84 which is coupled to the support member 80 via a drive pulley 86 and a drive belt 88. The drive belt 88 is anchored to the support 80 at 90. In use, the dispense probes 76 will be connected to an appropriate source of liquid to be dispensed into each of the storage wells 1-3 etc. while the aspirator probes 78 will be connected to a suitable vacuum source.

A liquid collection bath 92 extends beneath the path of the well holder 58 between a processing station 72 and waste removal station 74. Waste and other liquids are removed from the bath 92 via drain holes 120. In addition, at the processing station 72, a splash cover 94 is provided towards the outer side of the processing station.

At the waste removal station 74, a protective housing 96 is provided having a roof 98 and side walls 100,102. The roof 98 is inclined to the horizontal so that fluid will flow down the roof and walls and not drop back into the wells.

Operation of the module is controlled by a suitable controller (not shown) which selectively activates the stepper motors and actuator as required.

An example of a process using the module shown in FIGS. 5 to 7 will now be described with reference to FIG. 8.

Initially, the carrying tray or rack 20 is loaded into the rack or well holder 58 (step 150).

The stepper motor 42 is then activated to invert the well holder 58 and hence the storage wells 1-3 so that liquids in the wells are emptied out into the liquid collection bath 92. After a short delay, the stepper motor 42 is activated again to return the wells to their upright position (step 152).

The support 80 is then lowered towards the wells by suitably activating the stepper motor 84. A vacuum pump (not shown) attached to the aspirator probes 78 and a dispense pump (not shown) connected to the dispense probes 76 are then activated so that the wells can be filled with wash solution. The vacuum applied through the aspirator probes 78 ensures that the amount of wash solution in each well can be accurately controlled. After the wells have been filled, the dispense and vacuum pumps are switched off, the support 80 is raised and the process 152 is carried out to empty the wash liquid out of the wells. This process is then repeated a number, typically 3 to 5, of times (step 154).

The waste collection bath 92 underlies both the processing and waste removal stations and allows the vessel to be turned over and emptied at the processing station both 72,74 initially on entry (when containing test sample and associated reagents) and at the rinse stage.

The vessel can be turned upside down at the processing station 72 provided the speed of rotation is not so slow that fluid can run over the side of one well and into the next—to contaminate adjacent wells. The speed of rotation (through 180 degrees) is normally less than that required for spinning.

Flow into the adjacent well depends on various factors including the well profile (sidewall slope and height), fill level, fluid and material properties (viscosity/contact angle). These will govern the tilt angle at which fluid flow occurs. In the majority of situations the tilt angle at which fluid flows out and does not reach adjacent wells will be greater than 90°.

The actuator 70 is then activated under its pneumatic control to rotate the spinning mechanism and hence the well holder 58 to the waste removal station 74. A proximity switch (not shown) will indicate when the well holder 58 has reached the waste removal station and cause the pneumatic supply to be switched off (step 156).

The well holder 58 is then spun at a desired frequency and for a desired time by suitably activating the stepper motor 42 and is then stopped in its inverted position with the wells facing down (step 158). We have found that if the walls of the biochip well are tapered inwardly towards the biochip, this aids liquid removal.

Typical rotation frequencies are 900-2700 rpm, for durations of 6-15 seconds but that these are dependent on a variety of factors, including the well profile and biochip surface properties. In general higher spin speeds and longer spin times will create thinner films—the speed of rotation governing the degree of radial force applied. However very high spin rates may not be desirable as very thin films are likely to dry out more easily due to evaporation, potentially damaging the biochip surface. Accelerations are chosen to ensure that the speed of rotation is reached such that there is no overflow into adjacent wells or the fluid motion is not sufficiently rapid to damage the biochip surface. The direction of rotation can also be periodically reversed.

The pneumatic supply to the actuator 70 is then switched on so that the actuator 70 rotates the well holder back to the processing station 72, still in its inverted position and when a proximity switch (not shown) indicates that the well holder 58 has returned, the pneumatics are turned off. The stepper motor 42 is then activated to return the well holder 58 to its non-inverted position (step 160).

The carrying tray or rack 20 is then removed (step 162).

Figure 8:
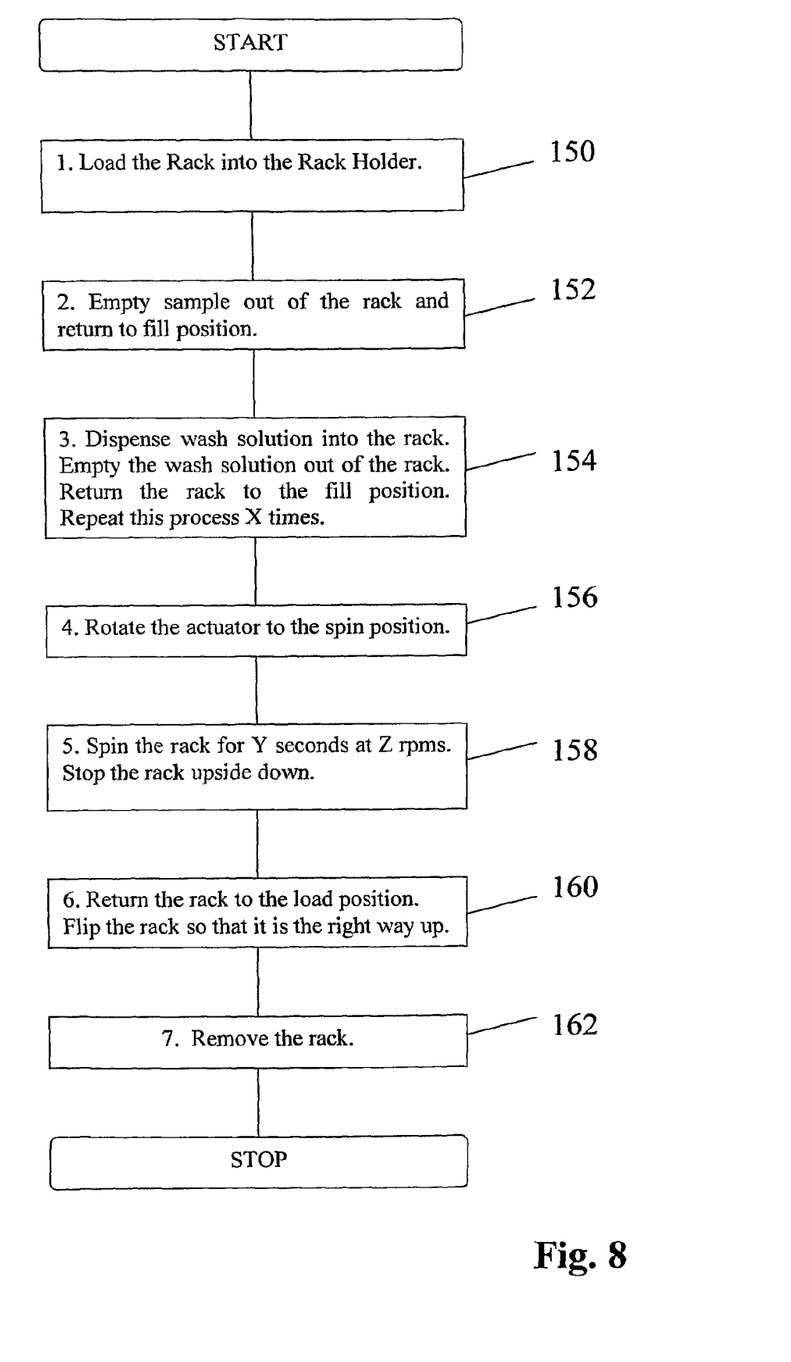
FIG. 8 is a flow diagram illustrating an example of a washing process.

It will be appreciated that other processes can be undertaken by this module and the process shown in FIG. 8 can be modified as necessary to aid in the soaking process and removal of unbound sample or reagent molecules. For example, during step 154, prior to emptying the wash solution out of the wells, the well holder 58 can be rocked to and fro by the stepper motor 42 to aid in the soaking process.

It should be understood that liquid will be ejected from the vessels during spinning if it is on the axis or on the side of the axis next the open top of the wells ie on the opposite side of the axis from the biochip surface. Liquid may also be ejected from the side of the axis away from the open top of the well provided the sidewalls slope outwards from this position towards the open top.

It will be appreciated that a number of advantages are achieved by this module. For example, it achieves efficient removal of sample, reagent and wash fluids from the storage wells above, to the side of, and below i.e. from around, the biochip. No contact between the biochip and the aspiration probe is required even at the edge of the chip between the chip and the side wall of the storage vessel. Furthermore, there is less chance of damage to the test sites on the biochip when compared to the use of aspiration probes lowered into the storage well, even at the side of the chip.

The invention claimed is:

1. An assay device processing apparatus comprising: a base, a rotatably mounted assay device vessel support; and a drive configured to rotate the support around a substantially horizontal first axis of the support, the horizontal first axis being parallel to the base, the support being rotatably mounted about the substantially horizontal first axis such that, upon rotation of the support, an assay device vessel attached to the support is rotated, wherein the support is movable between a processing station at which one or more liquids can be supplied to the vessel, and a waste removal station at which the support can be rotated to allow waste liquid(s) to disperse,
   wherein the support is also mounted for rotation about a vertical second axis to move from the processing station to the waste removal station.

2. The apparatus according to claim 1, wherein the waste removal station includes a protective housing within which the support is rotated in use about the first axis.

3. The apparatus according to claim 1, further comprising one or more dispense probes for delivering liquid to the assay device vessel attached to the support.

4. The apparatus according to claim 3, wherein the dispense probes and/or one or more aspiration probes are located at the processing station.

5. The apparatus according to claim 1, further comprising one or more aspiration probes for aspirating a liquid from the assay device vessel attached to the support.

6. The apparatus according to claim 1, wherein the first axis extends along or is adjacent to a base of an assay device vessel in use.

7. The apparatus according to claim 1, wherein the assay device vessel is attached to the support.

8. The apparatus according to claim 7, further comprising an assay device secured in the assay device vessel.

9. The apparatus according to claim 8, wherein the assay device is a biochip.

10. A method of processing an assay device in an assay device vessel containing a liquid and attached to a support of assay device processing apparatus, comprising a base, a rotatably mounted assay device vessel support; and a drive configured to rotate the support about a substantially horizontal first axis of the support, the horizontal first axis being parallel to the base the support being mounted for rotation about the substantially horizontal first axis such that, upon rotation of the support, an assay device vessel attached to the support is rotated, wherein the support is movable between a processing station at which one or more liquids can be supplied to the assay device vessel, and a waste removal station at which the support can be rotated to allow waste liquid(s) to disperse, the method comprising rotating the support about the first axis, wherein the support is also mounted for rotation about a vertical second axis to move from the processing station to the waste removal station.

11. The method according to claim 10, wherein the rotation about the first axis comprises a rotation that retains the liquid in the assay device vessel.

12. The method according to claim 10, wherein the rotation comprises inverting the assay device vessel.

13. The method according to claim 10, wherein the assay device vessel is spun about the first axis.

14. The method according to claim 13, wherein the assay device vessel is spun at a frequency in the range of 100-10000 rpm.

15. The method according to claim 13, wherein the assay device vessel is spun at a frequency in the range of 900-2700 rpm.

16. The method according to claim 10, the method further comprising moving the support with the assay device vessel attached to the waste removal station before carrying out the rotation.

17. The method according to claim 16, further comprising removing the assay device vessel, in a state in which the assay device vessel is inverted, from the waste removal station.

18. The method according to claim 10, wherein the liquid comprises a reagent for reacting with a species on the assay device.

19. The method according to claim 10, wherein the liquid comprises a wash solution.

20. The method according to claim 19, further comprising an assay device washing process that comprises supplying wash solution to the assay device vessel, and subsequently removing the wash solution and unbound sample or reagent molecules.

21. The method according to claim 20, wherein the removing the wash solution comprises spinning the assay device vessel.

22. The method according to claim 20, further comprising rocking the assay device vessel to and fro about the first axis prior to removing the wash solution and the unbound sample or reagent molecules.

* * * * *